United States Patent
Oosake et al.

(10) Patent No.: US 12,124,960 B2
(45) Date of Patent: *Oct. 22, 2024

(54) LEARNING APPARATUS AND LEARNING METHOD

(71) Applicant: FUJIFILM Corporation, Tokyo (JP)

(72) Inventors: Masaaki Oosake, Kanagawa (JP); Makoto Ozeki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 660 days.

This patent is subject to a terminal disclaimer.

(21) Appl. No.: 17/148,514

(22) Filed: Jan. 13, 2021

(65) Prior Publication Data

US 2021/0133473 A1 May 6, 2021

Related U.S. Application Data

(63) Continuation of application No. PCT/JP2019/026688, filed on Jul. 4, 2019.

(30) Foreign Application Priority Data

Jul. 26, 2018 (JP) .................................. 2018-140434

(51) Int. Cl.
*G06N 3/084* (2023.01)
*G06T 7/00* (2017.01)
(Continued)

(52) U.S. Cl.
CPC ............ *G06N 3/084* (2013.01); *G06T 7/0012* (2013.01); *G06V 10/143* (2022.01); *G06V 10/32* (2022.01);
(Continued)

(58) Field of Classification Search
CPC . G06T 2207/20084; G06T 2207/20081; G06T 5/00; G06T 7/00; G06T 7/70;
(Continued)

(56) References Cited

U.S. PATENT DOCUMENTS

| 10,629,185 | B2 | 4/2020 | Matsuda et al. |
| 2015/0134583 | A1* | 5/2015 | Tamatsu .................. G06N 3/08 706/25 |

(Continued)

FOREIGN PATENT DOCUMENTS

| JP | 2015102806 | 6/2015 |
| JP | 2016067780 | 5/2016 |

(Continued)

OTHER PUBLICATIONS

"Office Action of Japan Counterpart Application" with English translation thereof, issued on Nov. 19, 2021, p. 1-p. 8.

(Continued)

*Primary Examiner* — Margaret G Mastrodonato
(74) *Attorney, Agent, or Firm* — JCIPRNET

(57) ABSTRACT

An object of the present invention is to provide a learning apparatus and a learning method capable of appropriately learning pieces of data that belong to the same category and are acquired under different conditions. In a learning apparatus according a first aspect of the present invention, first data and second data are respectively input to a first input layer and a second input layer that are independent of each other, and feature quantities are calculated. Thus, the feature quantity calculation in one of the first and second input layers is not affected by the feature quantity calculation in the other input layer. In addition to feature extraction performed in the input layers, each of a first intermediate feature quantity calculation process and a second intermediate feature quantity calculation process is performed at least once in an intermediate layer that is shared by the first and second input layers. Thus, the feature quantities calculated from the first data and the second data in the respective input layers can be reflected in the intermediate feature quantity calculation in the intermediate layer. Consequently, pieces of data that belong to the same category and are (Continued)

acquired under different conditions can be appropriately learned.

16 Claims, 9 Drawing Sheets

(51) Int. Cl.
　　*G06V 10/143*　　(2022.01)
　　*G06V 10/32*　　(2022.01)
　　*G06V 10/44*　　(2022.01)
　　*G06V 10/60*　　(2022.01)
　　*G06V 10/764*　　(2022.01)
　　*G06V 10/776*　　(2022.01)
　　*G06V 10/82*　　(2022.01)

(52) U.S. Cl.
　　CPC ............ *G06V 10/454* (2022.01); *G06V 10/60* (2022.01); *G06V 10/764* (2022.01); *G06V 10/776* (2022.01); *G06V 10/82* (2022.01); *G06T 2207/20084* (2013.01); *G06V 2201/03* (2022.01)

(58) Field of Classification Search
　　CPC .... G06V 10/764; G06V 10/82; G06V 10/143; G06V 10/454; G06V 10/32; G06V 10/60; G06V 2201/03
　　See application file for complete search history.

(56) References Cited

U.S. PATENT DOCUMENTS

2017/0308773 A1　10/2017　Miyazaki et al.
2019/0034800 A1*　1/2019　Shiratani ................ G06N 3/042
2019/0244086 A1*　8/2019　Franca-Neto .......... G06N 3/063
2021/0133473 A1　5/2021　Oosake et al.
2022/0044406 A1*　2/2022　Spizhevoy .............. G06T 7/194

FOREIGN PATENT DOCUMENTS

JP　　2017199149　　11/2017
WO　　2017158575　　9/2017
WO　　2020022027　　1/2020

OTHER PUBLICATIONS

Ito, Hayato et al., "Classification of neoplasia and non-neoplasia for colon endocytoscopic images by convolutional neural network", IEICE Technical Report, Sep. 2017, submit with English abstract, pp. 1-7.
"International Search Report (Form PCT/ISA/210) of PCT/JP2019/026688," mailed on Oct. 1, 2019, with English translation thereof, pp. 1-5.
"Written Opinion of the International Searching Authority (Form PCT/ISA/237) of PCT/JP2019/026688," mailed on Oct. 1, 2019, with English translation thereof, pp. 1-10.
Sergey Ioffe et al., "Batch Normalization: Accelerating Deep Network Training by Reducing Internal Covariate Shift", Cornell University, arXiv:1502.03167v3, Mar. 2015, pp. 1-11.
"International Search Report (Form PCT/ISA/210) of PCT/JP2021/016004 of co-pending U.S. Appl. No. 18/165,934," mailed on Jul. 20, 2021, with English translation thereof, pp. 1-5.
"Written Opinion of the International Searching Authority (Form PCT/ISA/237) of PCT/JP2021/016004 of co-pending U.S. Appl. No. 18/165,934," mailed on Jul. 20, 2021, with English translation thereof, pp. 1-8.
"Office Action of Japan Counterpart Application", issued on Jun. 14, 2024, with English translation thereof, pp. 1-8.

* cited by examiner

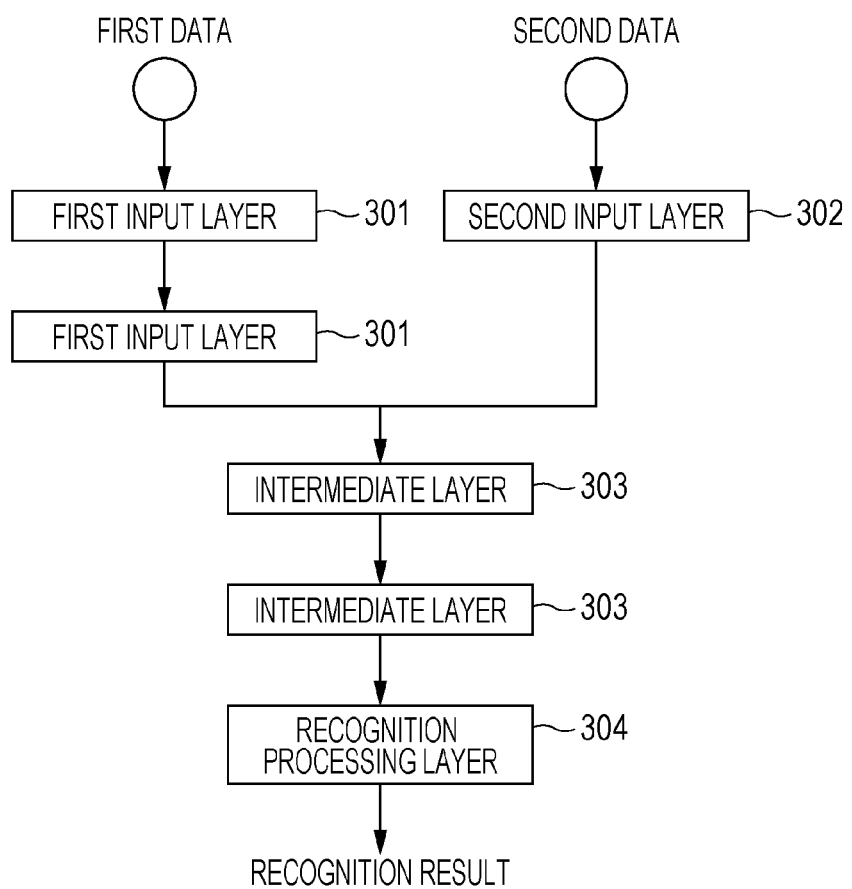

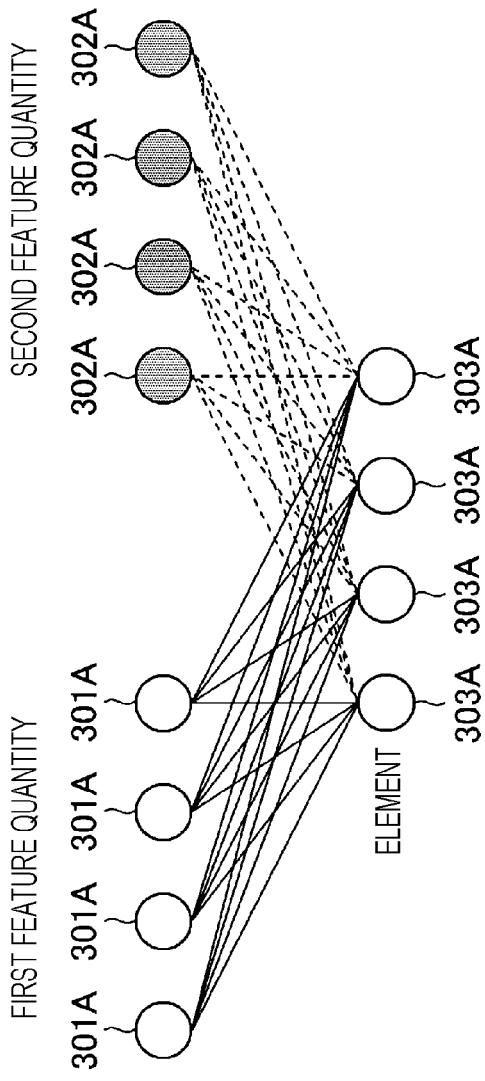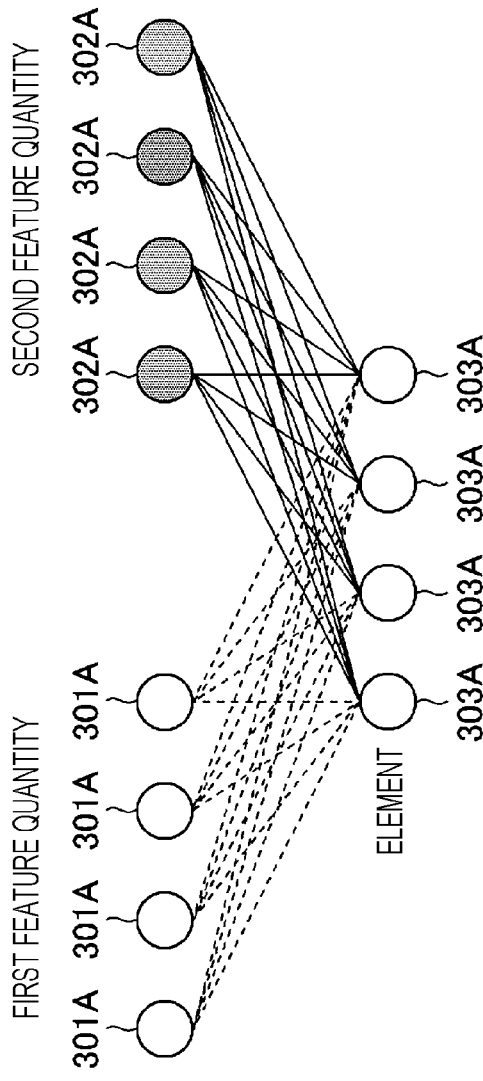

LEARNING APPARATUS AND LEARNING METHOD

CROSS-REFERENCE TO RELATED APPLICATIONS

The present application is a Continuation of PCT International Application No. PCT/JP2019/026688 filed on Jul. 4, 2019 claiming priority under 35 U.S.C § 119(a) to Japanese Patent Application No. 2018-140434 filed on Jul. 26, 2018. Each of the above applications is hereby expressly incorporated by reference, in its entirety, into the present application.

BACKGROUND OF THE INVENTION

1. Field of the Invention

The present invention relates to learning apparatuses and learning methods, and more particular to a learning apparatus and a learning method for performing machine learning using a hierarchical network.

2. Description of the Related Art

In the field of machine learning, it is known that learning is performed using a hierarchical network. A hierarchical network is generally constituted by a plurality of layers that perform feature extraction, recognition, and so on. There are various types in terms of specific network configurations and specific learning methods.

For example, JP2017-199149A describes a technique of inputting a plurality of pieces of data that belong to different categories (images and captions for the respective images) and causing a relationship to be learned. The images and the captions are input to different input layers.

SUMMARY OF THE INVENTION

In machine learning, there are cases where a plurality of pieces of data (data groups) that belong to the same category are acquired under different conditions and are used in learning. For example, there are cases where images are acquired using different imaging devices, at different imaging dates and times, for different photographic subjects, with different exposures, or the like. When the pieces of data thus acquired are learned, the fact that the pieces of data are acquired under different conditions is preferably and appropriately taken into account. In JP2017-199149A described above, however, data groups that belong to different categories are input. That is, the technique of JP2017-199149A is not a technique of inputting pieces of data that belong to the same category and have different acquisition conditions to perform learning.

As described above, with the technique of the related art, it is difficult to appropriately learn pieces of data that belong to the same category and that are acquired under different conditions.

The present invention has been made in view of such a circumstance and an object thereof is to provide a learning apparatus and a learning method capable of appropriately learning pieces of data that belong to the same category and that are acquired under different conditions.

To achieve the object described above, a learning apparatus according to a first aspect of the present invention is a learning apparatus including a hierarchical network. The hierarchical network includes a first input layer that receives first data and outputs a feature quantity, a second input layer that is independent of the first input layer and that receives second data and outputs a feature quantity, and an intermediate layer that is shared by the first input layer and the second input layer and that receives the feature quantity output by the first input layer or the feature quantity output by the second input layer and calculates another feature quantity. The first data is data selected from a first data group constituted by a plurality of pieces of data acquired under a first condition. The second data is data selected from a second data group constituted by a plurality of pieces of data which belong to a category identical to a category of the pieces of data constituting the first data group and which are acquired under a second condition different from the first condition. In the learning apparatus, each of a first intermediate feature quantity calculation process and a second intermediate feature quantity calculation process is performed at least once. The first intermediate feature quantity calculation process is a process in which a first feature quantity based on the feature quantity output from the first input layer is input to the intermediate layer and a first intermediate feature quantity is calculated in the intermediate layer. The second intermediate feature quantity calculation process is a process in which a second feature quantity based on the feature quantity output from the second input layer is input to the intermediate layer and a second intermediate feature quantity is calculated in the intermediate layer.

In the first aspect, the first data and the second data are respectively input to the first input layer and the second input layer that are independent of each other, and feature quantity is calculated in each of the first input layer and the second input layer. Thus, the feature quantity calculation in one of the first and second input layers is not affected by the feature quantity calculation in the other input layer. In addition, in the first aspect, in addition to the feature extraction performed in the input layers, each of the first intermediate feature quantity calculation process and the second intermediate feature quantity calculation process is performed at least once in the intermediate layer that is shared by the first input layer and the second input layer. Thus, the feature quantities respectively calculated from the first data and the second data in the respective input layers can be reflected in the intermediate feature quantity calculation in the intermediate layer. In addition, since a hierarchical network involves many parameters, overlearning is likely to occur. However, overlearning can be avoided by providing a large amount of data. In the learning apparatus according to the first aspect, learning can be performed in the intermediate layer using a large amount of data including both the first data and the second data. Thus, overlearning is unlikely to occur. On the other hand, since the input layer is configured as the first input layer and the second input layer which are independent of each other, the number of parameters of each input layer reduces. Thus, overlearning is unlikely to occur even with a small amount of data.

According to the first aspect, pieces of data that belong to the same category and are acquired under different conditions can be appropriately learned in this manner.

In the first aspect and each aspect below, as for "the first feature quantity based on the feature quantity output from the first input layer and the second feature quantity based on the feature quantity output from the second input layer", the feature quantity output by the first input layer and the feature quantity output by the second input layer may be respectively input as the first feature quantity and the second feature quantity without any processing. Alternatively, a feature quantity obtained by performing some kind of processing on the feature quantity output by the first input layer and a feature quantity obtained by performing some kind of processing on the feature quantity output by the second input layer may be respectively input as the first feature quantity and the second feature quantity. In addition, "belonging to the identical category" indicates a combination of an image and an image, text and text, or sound and sound. "The first condition and the second condition being different" excludes "classifying pieces of data acquired under the same condition into two".

In the first aspect and each aspect below, each of the first input layer, the second input layer, and the intermediate layer may be constituted by a single layer or by a plurality of layers. In addition, the number of layers constituting the first input layer and the number of layers constituting the second input layer may be the same or different. The hierarchical network may include an output layer, a recognition layer, or the like in addition to the first input layer, the second input layer, and the intermediate layer.

In addition, in the first aspect and each aspect below, the number of layers of the first input layer, the number of layers of the second input layer, and parameters in each layer are preferably adjusted in consideration of a result of learning (for example, an error or loss between a recognition result and correct answer data, or the like) so that the feature quantity output from the first input layer and the feature quantity output from the second input layer can appropriately express features of the first data and the second data, respectively. Further, as for the intermediate layer, the number of layers of the intermediate layer and the parameters in each layer are preferably adjusted similarly in consideration of the result of learning.

In a learning apparatus according to a second aspect, in the first aspect, the first intermediate feature quantity calculation process is performed at least twice, and the second intermediate feature quantity calculation process is performed in a period from an end of the first intermediate feature quantity calculation process to a start of the other first intermediate feature quantity calculation process. In a case where the first intermediate feature quantity calculation process is successively performed multiple times and then the second intermediate feature quantity calculation process is performed, the feature quantity calculated in the intermediate layer may be strongly affected by the first data and learning (calculation of the feature quantity) is possibly not appropriately performed for the second data (the same applies to the opposite case). Therefore, in the second aspect, the second intermediate feature quantity calculation process is performed in the period from the end of the first intermediate feature quantity calculation process to the start of the other first intermediate feature quantity calculation process. Consequently, a circumstance in which the feature quantity calculated in the second intermediate feature quantity calculation process is excessively affected by the first data is avoided, and learning can be appropriately performed for the first data and the second data.

In a learning apparatus according to a third embodiment, in the first or second aspect, the first intermediate feature quantity calculation process is performed at least twice, and the second intermediate feature quantity calculation process is performed after the first intermediate feature quantity calculation processes are ended at least twice. In the third aspect, similarly to the second aspect described above, a circumstance in which the feature quantity calculated in the second intermediate feature quantity calculation process is excessively affected by the first data is avoided, and learning can be appropriately performed for the first data and the second data.

In a learning apparatus according to a fourth aspect, in any one of the first to third aspects, the hierarchical network is a convolutional neural network. The fourth aspect defines an example of the specific configuration of the hierarchical network.

In a learning apparatus according to a fifth aspect, in any one of the first to fourth aspects, the first input layer and/or the second input layer calculates the feature quantity through a convolutional operation. The fifth aspect defines one configuration of the specific method of calculating the feature quantity in the first input layer or the second input layer.

In a learning apparatus according to a sixth aspect, in any one of the first to fifth aspects, the first input layer and/or the second input layer calculates the feature quantity through a pooling process. The sixth aspect defines one configuration of the specific method of calculating the feature quantity in the first input layer or the second input layer.

In a learning apparatus according to a seventh aspect, in any one of the first to sixth aspects, the first input layer and/or the second input layer calculates the feature quantity through a batch normalization process. The seventh aspect defines one configuration of the specific method of calculating the feature quantity in the first input layer or the second input layer.

In a learning apparatus according to an eighth aspect, in any one of the first to seventh aspects, the intermediate layer calculates the feature quantity through a convolutional operation. The eighth aspect defines one configuration of the specific method of calculating the feature quantity.

In a learning apparatus according to a ninth aspect, in any one of the first to eighth aspects, the intermediate layer calculates the feature quantity through a pooling process. The ninth aspect defines one configuration of the specific method of calculating the feature quantity.

In a learning apparatus according to a tenth aspect, in any one of the first to ninth aspects, the intermediate layer calculates the feature quantity through a batch normalization process. The tenth aspect defines one configuration of the specific method of calculating the feature quantity.

In a learning apparatus according to an eleventh aspect, in any one of the first to tenth aspects, the first input layer receives, as the first data, first image data acquired under the first condition, and the second input layer receives, as the second data, second image data acquired under the second condition different from the first condition. The eleventh aspect defines an example of the specific configurations of the first input data and the second input data. Even pieces of image data acquired under different conditions (an example of pieces of data that belong to the identical category) can be input to the first input layer and the second input layer, and the first intermediate feature quantity calculation process and the second intermediate feature quantity calculation process can be performed. In this manner, learning can be appropriately performed.

In a learning apparatus according to a twelfth aspect, in the eleventh aspect, the first condition and the second condition are different in at least one of an imaging device, a wavelength balance of observation light, a resolution, or image processing to be performed on an image. The twelfth aspect defines one configuration of the difference between the first condition and the second condition. Note that in the twelfth aspect, it is assumed that "being different in an imaging device" means that "modalities are the same but the models, model numbers, performances, or the like are different". For example, an endoscope apparatus and a computed tomography (CT) apparatus are different modalities. In addition, "being different in a wavelength balance of observation light" means that the wavelength ranges of the observation light and/or the relative relationship between intensities in the respective wavelength ranges of the observation light are different. In addition, "being different in image processing to be performed on an image" includes, but is not limited to, processing for emphasizing or reducing the influence of a specific wavelength component, or processing for making a specific target or region to be emphasized or less conspicuous.

In a learning apparatus according to a thirteenth aspect, in the twelfth aspect, the first input layer receives, as the first image data, first medical image data acquired using first observation light, and the second input layer receives, as the second image data, second medical image data acquired using second observation light different from the first observation light in the wavelength balance. "Which structure of a photographic subject is clearly (or indistinctly) depicted in a captured image" depends on the wavelength balance of the observation light used for imaging. Thus, there are cases where images are acquired using a plurality of types of observation light having different wavelength balances in a scene of diagnosis or examination. However, in the thirteenth aspect, learning of images can be appropriately performed even in such a case. Note that in the thirteenth aspect and each aspect below, the "medical image" is also referred to as an "image for medical use".

In a learning apparatus according to a fourteenth aspect, in the thirteenth aspect, the first input layer receives, as the first image data, the first medical image data acquired using white light as the first observation light, and the second input layer receives, as the second image data, the second medical image data acquired using narrow-band light as the second observation light. When medical images are acquired, the images are often acquired using white light as observation light to allow for visual check by a user. On the other hand, in the case of the narrow-band light, a structure different from that of the white-light image, such as a detail or a deep portion of the subject, can be observed depending on the wavelength. However, since the narrow-band light is not suitable for visual observation, the number of images acquired is smaller than the number of white-light images. In the fourteenth aspect, learning can be appropriately performed even in such a case. Note that in the fourteenth aspect, the "narrow-band light" may be observation light having a short wavelength such as blue light or violet light, or may be observation light having a long wavelength such as red light or infrared light.

In a learning apparatus according to a fifteenth aspect, in the thirteenth aspect, the first input layer receives, as the first image data, the first medical image data acquired using first narrow-band light as the first observation light, and the second input layer receives, as the second image data, the second medical image data acquired using, as the second observation light, second narrow-band light different from the first narrow-band light. When medical images are acquired, a plurality of kinds of narrow-band light may be used as the observation light to acquire images depending on the usage of the images. According to the fifteenth aspect, learning can be appropriately performed even in such a case. Note that "the second narrow-band light different from the first narrow-band light" means that the first narrow-band light and the second narrow-band light are different in the wavelength range of the observation light and/or the intensity of the observation light.

To achieve the object described above, a learning method according to a sixteenth aspect of the present invention is a learning method for a learning apparatus including a hierarchical network. The hierarchical network includes a first input layer that receives first data and outputs a feature quantity, a second input layer that is independent of the first input layer and that receives second data and outputs a feature quantity, and an intermediate layer that is shared by the first input layer and the second input layer and that receives the feature quantity output by the first input layer or the feature quantity output by the second input layer and calculates another feature quantity. The first data is data selected from a first data group constituted by a plurality of pieces of data acquired under a first condition. The second data is data selected from a second data group constituted by a plurality of pieces of data which belong to a category identical to a category of the pieces of data constituting the first data group and which are acquired under a second condition different from the first condition. The learning method includes: a first feature quantity calculation step of inputting a first feature quantity based on the feature quantity output from the first input layer to the intermediate layer and calculating a first intermediate feature quantity in the intermediate layer; and a second intermediate feature quantity calculation step of inputting a second feature quantity based on the feature quantity output from the second input layer to the intermediate layer and calculating a second intermediate feature quantity in the intermediate layer, and each of the first intermediate feature quantity calculation step and the second intermediate feature quantity calculation step is performed at least once. According to the sixteenth aspect, pieces of data that belong to the same category and are acquired under different conditions can be appropriately learned as in the first aspect.

The learning method according to the sixteenth aspect may further include configurations similar to those of the second to fifteenth aspects. In addition, aspects of the present invention include a program for causing a learning apparatus to perform the learning method according to those aspects and a non-transitory recording medium in which a computer-readable code of the program is recorded.

As described above, with the learning apparatus and the learning method according to the aspects of the present disclosure, pieces of data that belong to the same category and are acquired under different conditions can be appropriately learned.

BRIEF DESCRIPTION OF THE DRAWINGS

FIG. 4 is a diagram illustrating still another example of the configuration of the hierarchical network;

FIGS. 6A and 6B are diagrams illustrating how a feature quantity to be input to an intermediate layer is switched;

DESCRIPTION OF THE PREFERRED EMBODIMENTS

Embodiments of a learning apparatus and a learning method according to embodiments of the present disclosure will be described in detail below with reference to the accompanying drawings.

Embodiment

<Configuration of Learning System>

Figure 1:
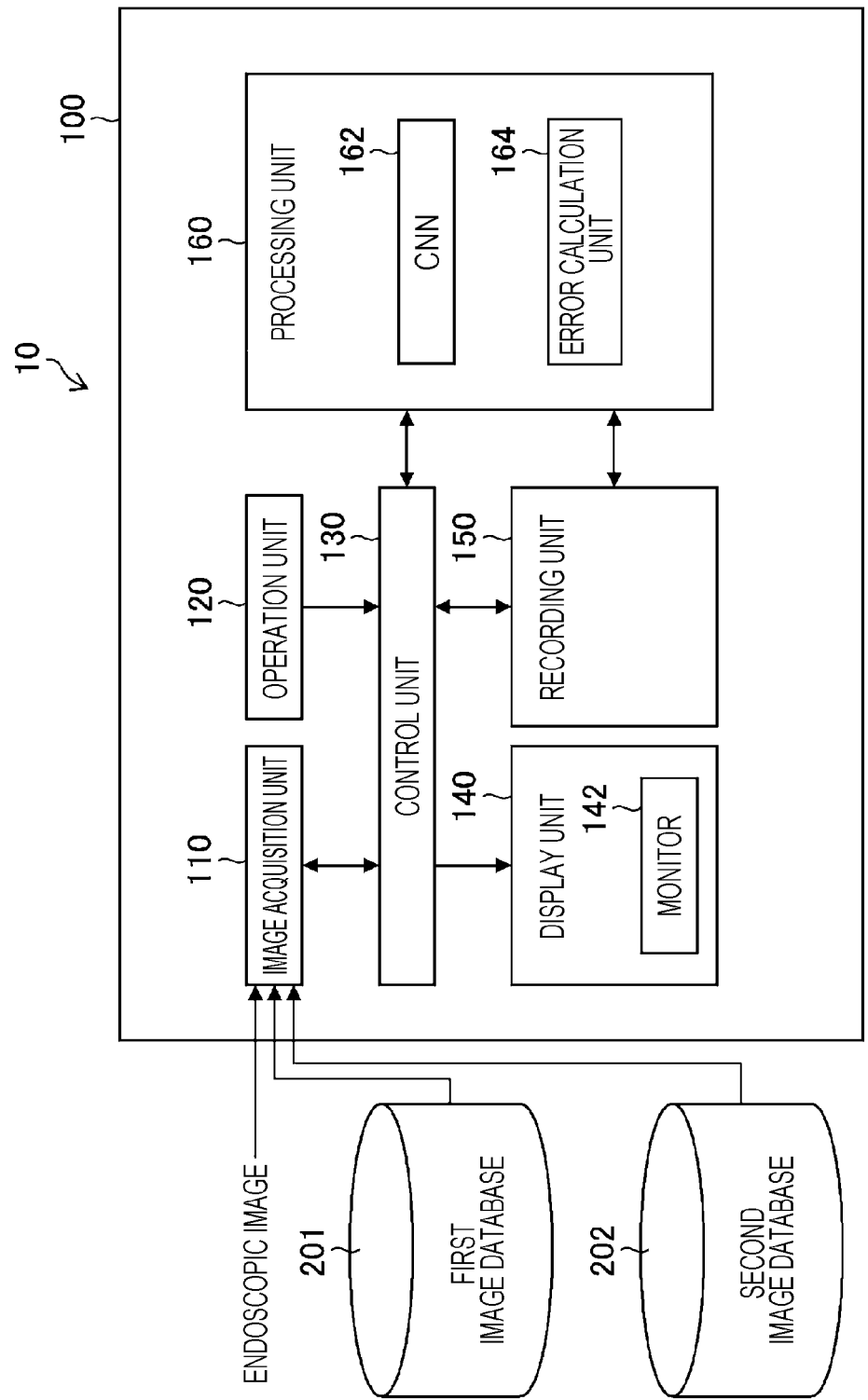
FIG. 1 is a diagram illustrating a configuration of a learning system according to an embodiment.

FIG. 1 is a block diagram illustrating a configuration of a learning system 10 (learning apparatus) according to an embodiment. The learning system 10 includes a learning recognition apparatus 100 (learning apparatus), a first image database 201, and a second image database 202. The learning recognition apparatus 100 performs a learning process and a recognition process that are based on images captured with an endoscope that is inserted into a subject. In the first image database 201, a plurality of endoscopic images acquired using normal light (white light) as observation light are recorded. In the second image database 202, a plurality of endoscopic images acquired using special light (narrow-band light) as observation light are recorded. Note that in the following description, an image acquired using normal light (white light) as observation light is referred to as a "normal-light image" (or "white-light image"), and an image acquired using special light (narrow-band light) as observation light is referred to as a "special-light image" (or "narrow-band-light image"). The endoscopic images recorded in the first image database 201 and the second image database 202 are an example of medical images (also referred to as images for medical use).

<First Image Database and Second Image Database>
<Normal-Light Images and Special-Light Images>

The first image database 201 and the second image database 202 are constituted by a recording medium such as a hard disk. In the first image database 201, a plurality of normal-light images (first data group, first data, first image data, or first medical images) captured using the normal light as the observation light (first observation light) are recorded. In the second image database 202, a plurality of special-light images (second data group, second data, second image data, or second medical images) captured using the special light as the observation light (second observation light) are recorded. That is, the plurality of normal-light images recorded in the first image database 201 are an aspect of a "plurality of pieces of data acquired under a first condition" in the present disclosure, and the plurality of special-light images recorded in the second image database 202 are an aspect of a "plurality of pieces of data acquired under a second condition different from the first condition" in the present disclosure. The special light (narrow-band light) used for capturing special-light images can be, for example, narrow-band blue light. Alternatively, the special light may be of another wavelength such as narrow-band red light. In addition, the case where the first observation light and the second observation light are the white light and the narrow-band light, respectively, has been described in the example above. However, medical images such as endoscopic images may be used which are acquired using, as the observation light, first narrow-band light and second narrow-band light that are different in a wavelength range and/or intensity.

An acquisition condition (first condition) of the normal-light images and an acquisition condition (second condition) of the special-light images are different in the wavelength balance of the observation light in this manner. In addition to this, the acquisition condition of the normal-light images and the acquisition condition of the special-light images may be different in an imaging device, a resolution, and image processing to be performed on an image. That is, the first condition and the second condition may be different in at least one of the imaging device, the wavelength balance of the observation light, the resolution, or the image processing to be performed on an image. "Being different in the imaging device" includes, but is not limited to, using endoscopes having different optical system characteristics or different processor performances. In addition, "being different in the image processing to be performed on an image" includes, but is not limited to, the presence or absence of processing for making a specific region such as a region of interest to be emphasized or less conspicuous or processing for emphasizing or reducing the influence of a specific wavelength component and/or degrees of such processing being different.

<Difference in Number of Pieces of Data Depending on Data Acquisition Condition>

When a user performs observation or examination using an endoscope, it is often the case that the user displays an image acquired using the normal light (white light) as the observation light on a monitor to check the image. Depending on the purpose and circumstance of the observation or examination (for example, it is difficult to observe the structure of a lesion with the normal light), there may be a case where an image is acquired using the special light such as the narrow-band light as the observation light. However, the frequency with which the special light is used as the observation light is less than that of the normal light. Thus, it is often the case that the number of special-light images is significantly smaller than the number of normal-light images. When learning and/or recognition of images are performed through machine learning, learning and/or recognition needs to be performed for the special-light images. However, if the number of pieces of data of the special-light images is small, the accuracy of learning and/or recognition may decrease compared with that of the normal-light images. In view of such a circumstance, in the embodiment, a hierarchical network configuration (described later) and an intermediate feature quantity calculation process (described later) are adopted to enable learning and/or recognition to be appropriately performed even in a circumstance in which there is a difference between the numbers of pieces of data.

<Correct Answer Data of Endoscopic Images>

The first image database 201 and the second image database 202 store, in addition to endoscopic images described above, "correct answer data" for identifying a region of interest (ROI) in association with the images. Specifically, the first image database 201 stores a plurality of pieces of correct answer data each corresponding to a corresponding one of a plurality of normal-light images. The second image database 202 stores a plurality of pieces of correct answer data each corresponding to a corresponding one of a plurality of special-light images. The correct answer data is preferably a region of interest or a discrimination result designated by a doctor for individual endoscopic images.

<Configuration of Learning Recognition Apparatus>

An image acquisition unit 110 is constituted by an apparatus or the like that communicates with an external server, a database, or the like via a network. The image acquisition unit 110 acquires endoscopic images and pieces of correct answer data for use in learning and recognition from the first image database 201 and the second image database 202. The image acquisition unit 110 is also capable of acquiring endoscopic images from an endoscope system, a hospital server, or the like connected to the learning system 10 via a network (not illustrated). An operation unit 120 includes input devices such as a keyboard (not illustrated) and a mouse (not illustrated). A user is able to perform operations necessary for processing such as image acquisition, learning, and recognition via these devices. A control unit 130 reads various programs recorded in a recording unit 150 and controls the operation of the entire learning system 10 in accordance with a command input from the operation unit 120. The control unit 130 also back-propagates an error (loss) calculated by an error calculation unit 164 (described later) to a convolutional neural network (CNN) 162 to update weight parameters of the CNN 162.

A display unit 140 includes a monitor 142 (display device). The display unit 140 displays an endoscopic image, a learning result, a recognition result, a processing condition setting screen, and so on. The recording unit 150 is constituted by a read-only memory (ROM) (not illustrated), a random access memory (RAM) (not illustrated), a hard disk (not illustrated), or the like. The recording unit 150 records therein data acquired by the image acquisition unit 110, the learning result and the recognition result obtained by a processing unit 160, and so on. The recording unit 150 also records therein programs for performing learning and recognition of endoscopic images (medical images) (which include a program for causing the learning system 10 to perform a learning method according to the present disclosure). The processing unit 160 includes the CNN 162 which is a hierarchical network, and the error calculation unit 164 that calculates a loss (error) on the basis of the output (recognition result) of the CNN 162 and the "correct answer data" described above.

<Layer Configuration of CNN>

Figure 2:
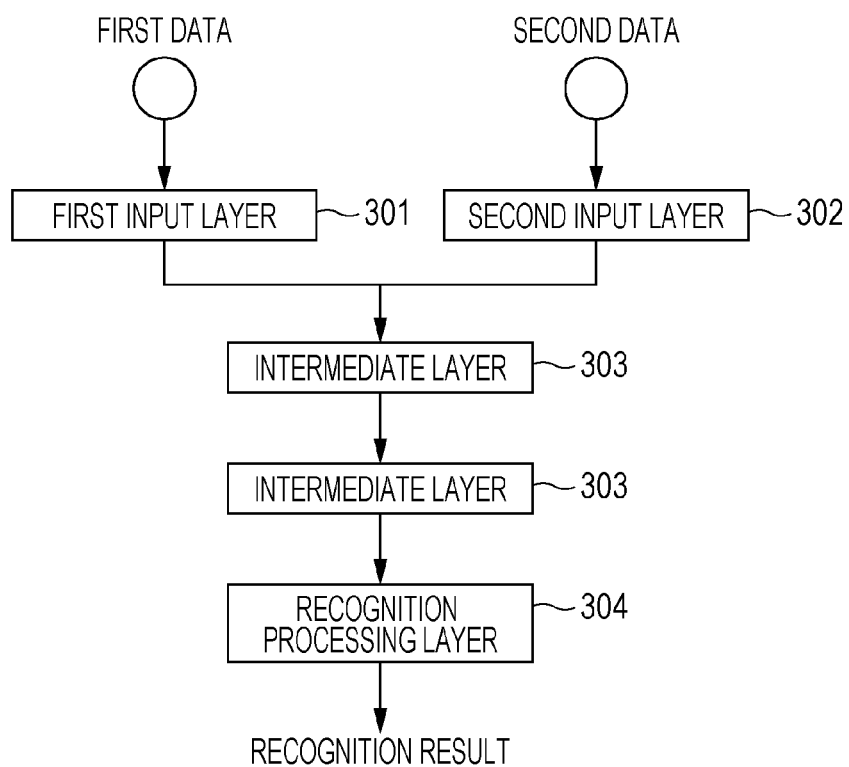
FIG. 2 is a diagram illustrating an example of a configuration of a hierarchical network.

FIG. 2 is a diagram illustrating an example of a layer configuration of the CNN 162. In the example illustrated in FIG. 2, the CNN 162 includes a first input layer 301 (first input layer), a second input layer 302 (second input layer), two intermediate layers 303 (intermediate layers), and a recognition processing layer 304. The first input layer 301 receives an image (first data) selected from among the normal-light images (first data group) stored in the first image database 201 and outputs a feature quantity. The second input layer 302 is an input layer that is independent of the first input layer 301. The second input layer 302 receives an image (second data) selected from among the special-light images (second data group) stored in the second image database 202 and outputs a feature quantity. The intermediate layer 303 is an intermediate layer shared by the first input layer 301 and the second input layer 302. The intermediate layer 303 receives the feature quantity output by the first input layer 301 or the feature quantity output by the second input layer and calculates another feature quantity (first intermediate feature quantity, second intermediate feature quantity). These layers have a structure in which a plurality of "nodes" are connected to each other by "edges" and hold a plurality of weight parameters. The values of the weight parameters change as learning progresses.

<Processing in Input Layers and Intermediate Layers>

The first input layer 301, the second input layer 302, and the intermediate layers 303 calculate feature quantities through a convolutional operation, a pooling process, and batch normalization process. The convolutional operation is a process of acquiring a feature map through a convolutional operation using a filter, and plays a role of extracting features such as extracting edges from an image. Through this convolutional operation using a filter, one channel of "feature map" (one feature map) is generated for one filter. The size of the "feature map" is downscaled by convolution and reduces as the convolution is performed at each layer. Ultimately, one "feature map" having a size equal to that of the input image is obtained. The pooling process is a process of reducing (or enlarging) the feature map output as a result of the convolutional operation to obtain a new feature map, and plays a role of providing robustness so that the extracted features are not affected by translation or the like. The batch normalization process is a process of normalizing the distribution of data in units of minibatches used when learning is performed, and plays a role of making learning progress fast, reducing dependency on an initial value, suppressing overlearning, and the like. Each of the first input layer 301, the second input layer 302, and the intermediate layers 303 can be constituted by one or a plurality of layers that perform these processes. Note that the layer configuration is not limited to the case where a configuration includes one layer for performing the convolutional operation, one layer for performing the pooling process, and one layer for performing the batch normalization process, and a plurality layers for any of the processes (for example, a plurality of layers for performing the convolutional operation) may be included.

Among these layers of the first input layer 301, the second input layer 302, and the intermediate layers 303, lower-order feature extraction (such as edge extraction) is performed in a layer close to the input side, and higher-order feature extraction (extraction of features relating to the shape, the structure, or the like of a target) is performed as the layer approaches the output side. In the intermediate layers 303, segmentation of the target (region of interest) is performed on the basis of the feature quantities extracted in the first input layer 301 and the second input layer 302.

<Processing in Recognition Processing Layer>

The recognition processing layer 304 is a layer that detects the location of a region of interest depicted in an input image (normal-light image, special-light image) on the basis of the feature quantity output from the intermediate layer 303 and outputs the result. The recognition processing layer 304 grasps the location of the region of interest depicted in the image at the pixel level in accordance with the "feature map" obtained from the intermediate layer 303. That is, the recognition processing layer 304 is capable of detecting whether each pixel of the endoscopic image belongs to the region of interest and outputting the detection result.

The recognition processing layer 304 may perform discrimination of a lesion and output the discrimination result. For example, the recognition processing layer 304 may classify endoscopic images into three categories of "tumorous", "non-tumorous", and "others", and may output three scores (the sum of the three scores is equal to 100%) corresponding to "tumorous", "non-tumorous", and "others" as the discrimination result. Alternatively, the recognition processing layer 304 may output the classification result when the endoscopic images can be clearly classified on the basis of the three scores. Note that when the recognition processing layer 304 outputs the discrimination result, the recognition processing layer 304 preferably has a fully connected layer as a single last layer or fully connected layers as a plurality of last layers.

<Layer Configuration of CNN (Other Examples)>

Figure 3:
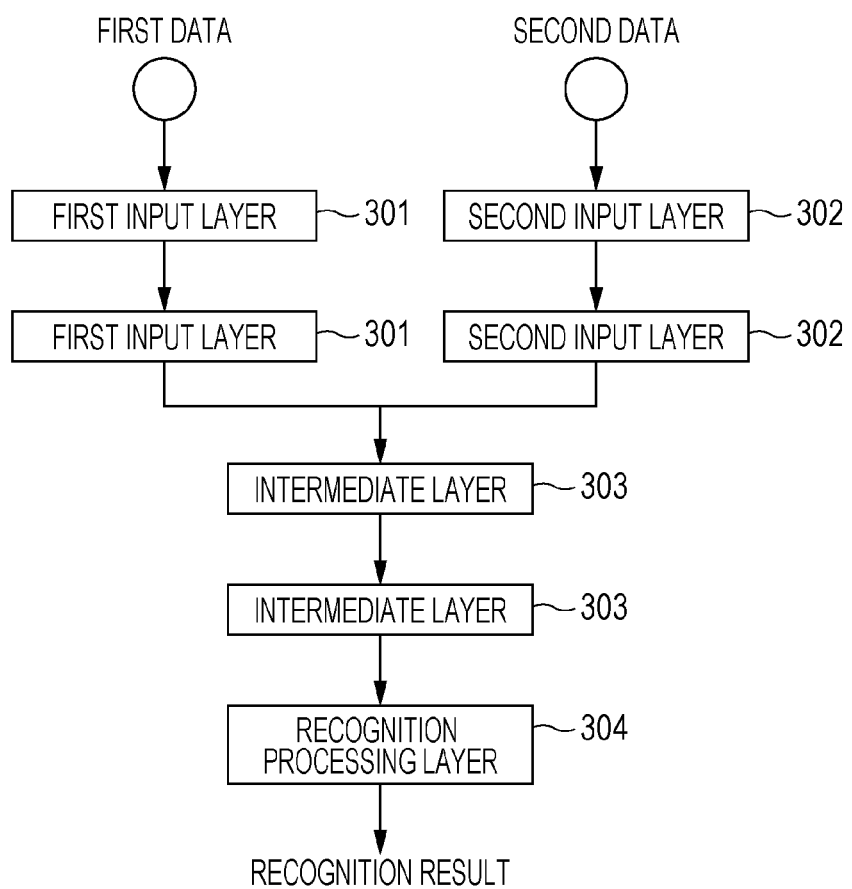
FIG. 3 is a diagram illustrating another example of the configuration of the hierarchical network.

FIG. 3 is a diagram illustrating another example of the layer configuration of the CNN 162. In the example illustrated in FIG. 3, the CNN 162 includes two first input layers 301 (first input layers), two second input layers 302 (second input layers), two intermediate layers 303 (intermediate layers), and a recognition processing layer 304. Thus, the CNN 162 may include the plurality of first input layers 301, the plurality of second input layers 302, and the plurality of intermediate layers 303.

FIG. 4 is a diagram illustrating still another example of the layer configuration of the CNN 162. In the example illustrated in FIG. 4, the CNN 162 includes two first input layers 301 (first input layers), a second input layer 302 (second input layer), two intermediate layers 303 (intermediate layers), and a recognition processing layer 304. The number of first input layers 301 and the number of second input layers 302 may be different from each other as in the example of FIG. 4. The number of first input layers and the number of second input layers can be set so that the feature quantities of the respective input pieces of data are appropriately extracted. In relation to the examples illustrated in FIGS. 3 and 4, the layer configuration of the individual layers and the content of the processing (the convolutional operation, the pooling process, and the batch normalization process) are substantially the same as those described above for the example illustrated in FIG. 2. A specific procedure of a learning method using the CNN 162 having the configurations illustrated in FIGS. 2 to 4 will be described in detail below.

<Implementation of Functions with Various Processors>

Functions of the image acquisition unit 110, the control unit 130, and the processing unit 160 (the CNN 162 and the error calculation unit 164) described above can be implemented using various processors. The various processors include, for example, a central processing unit (CPU) which is a general-purpose processor that executes software (program) to implement various functions. In addition, the various processors mentioned above include a graphics processing unit (GPU) which is a processor specialized for image processing and a programmable logic device (PLD) which is a processor whose circuit configuration is changeable after manufacture, such as a field programmable gate array (FPGA). Further, the various processors mentioned above include a dedicated electric circuitry which is a processor having a circuit configuration designed exclusively for executing a specific process, such as an application-specific integrated circuit (ASIC).

The function of each unit may be implemented by a single processor, or may be implemented by a plurality of processors of the same kind or of different kinds (for example, a plurality of FPGAs, a combination of a CPU and an FPGA, or a combination of a CPU and a GPU). In addition, the plurality of functions may be implemented by a single processor. Examples in which the plurality of functions are configured using a single processor include a first configuration, as exemplified by a computer, in which a combination of one or more CPUs and software constitutes a single processor and this processor implements the plurality of functions. The examples also include a second configuration, as exemplified by a system on a chip (SoC) or the like, in which a processor that implements the functions of the entire system with a single integrated circuit (IC) chip is used. As described above, the various functions are configured using one or more of the various processors described above in terms of the hardware structure. Further, the hardware structure of these various processors is, more specifically, electric circuitry in which circuit elements such as semiconductor elements are combined.

When the above-described processor or electric circuitry executes software (program), the processor (computer)-readable code of the software to be executed is stored in a non-transitory recording medium such as a read-only memory (ROM), and the processor refers to the software. The software stored in the non-transitory recording medium includes a program for performing the learning method according to the present disclosure. The code may be recorded in a non-transitory recording media such as various magneto-optical recording apparatuses or a semiconductor memory, instead of the ROM. When processing using software is performed, for example, a random access memory (RAM) is used as a temporary storage area. In addition, reference can be made to data stored in, for example, an electronically erasable and programmable read-only memory (EEPROM) (not illustrated). As the ROM, the RAM, or the EEPROM, a recording medium included in the recording unit 150 may be used.

<Learning Method>

In the learning system 10 having the above-described configuration, each of a first intermediate feature quantity calculation process and a second intermediate feature quantity calculation process is performed at least once. The first intermediate feature quantity calculation process is a process in which a first feature quantity based on a feature quantity output from the first input layer 301 is input to the intermediate layer 303 and a first intermediate feature quantity is calculated in the intermediate layer 303. The second intermediate feature quantity calculation process is a process in which a second feature quantity based on a feature quantity output from the second input layer 302 is input to the intermediate layer 303 and a second intermediate feature quantity is calculated in the intermediate layer 303.

<First Intermediate Feature Quantity Calculation Process>

Figure 5A:
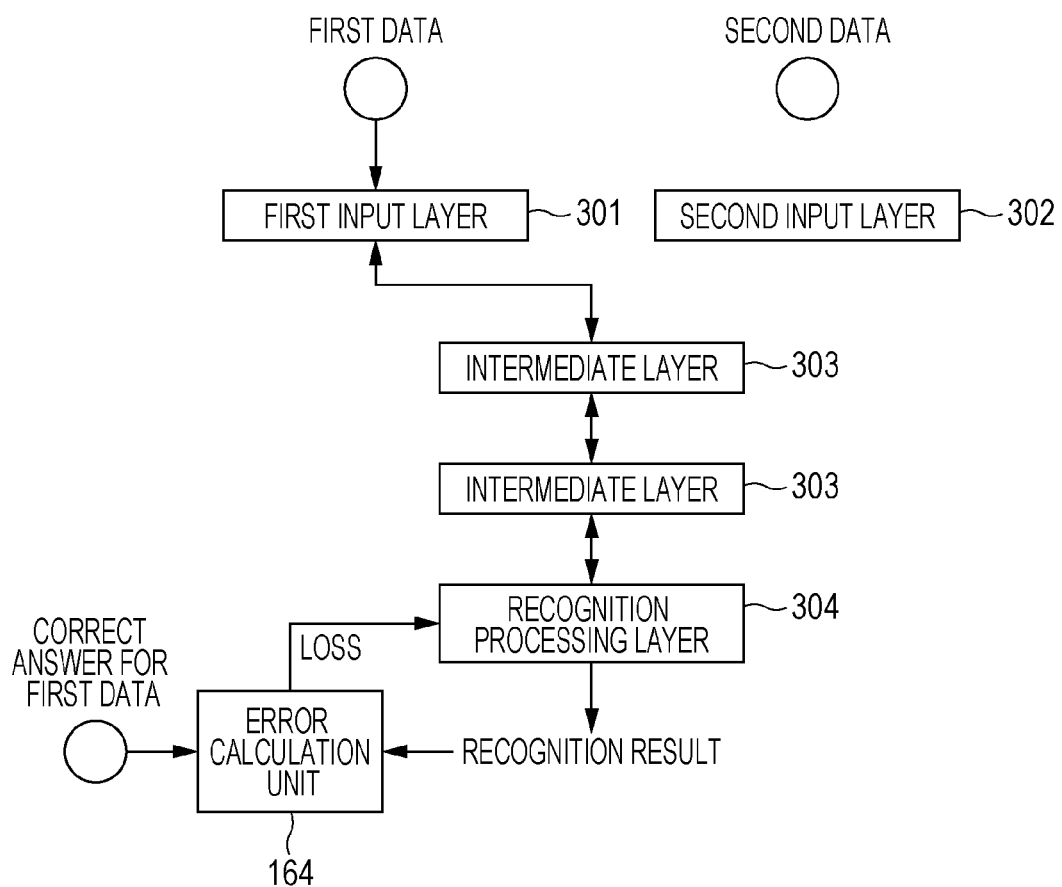
FIGS. 5A and 5B are diagrams illustrating how learning is performed using first data and second data.
Figure 5B:
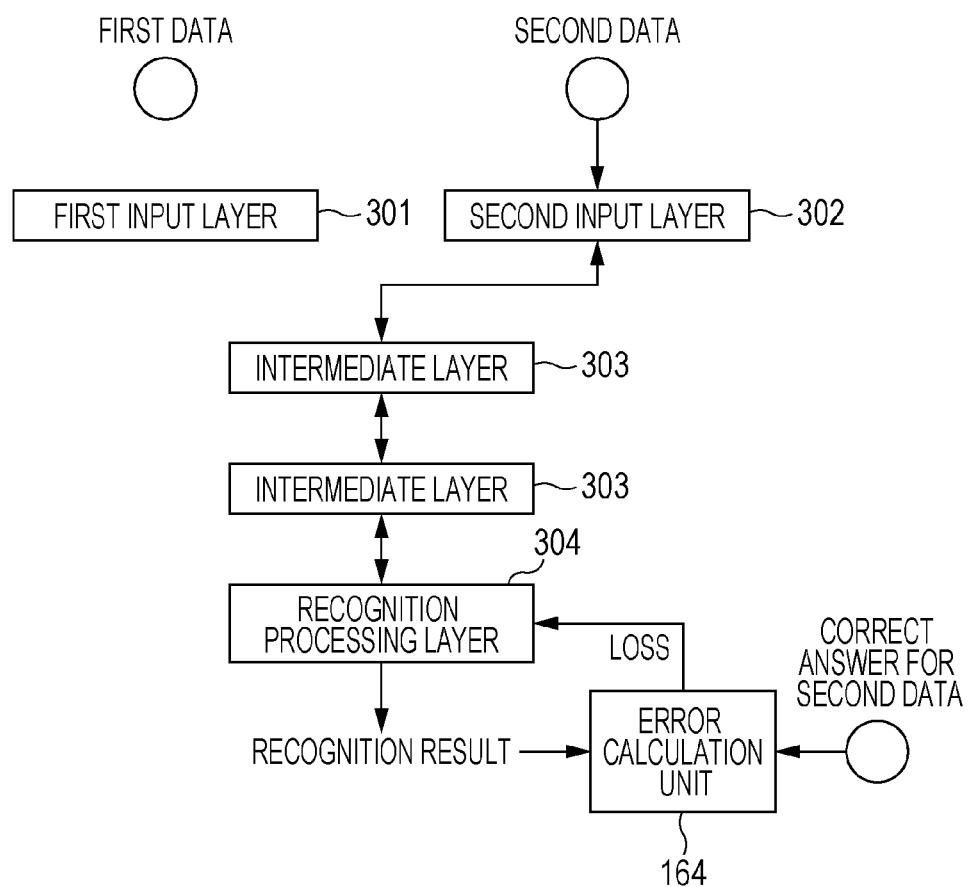

In the first intermediate feature quantity calculation process, a minibatch is formed using a plurality of images (first data) selected from among the plurality of normal-light images recorded in the first image database 201, and the minibatch is input to the first input layer 301. Since the first input layer 301 and the second input layer 302 are connected to the intermediate layer 303 as described above, the output of the first input layer 301 and the output of the second input layer 302 are input in a switching manner when learning is performed. FIGS. 5A and 5B are diagram illustrating how the output is switched. FIG. 5A illustrates a state in which the output from the first input layer 301 is input to the intermediate layer 303. Note that in FIGS. 5A and 5B, a downward arrow indicates that information is transmitted in a direction from the first input layer 301 or the second input layer 302 to the recognition processing layer 304 via the intermediate layers 303 (in a learning direction), and an upward arrow opposite to the learning direction indicates that information is transmitted from the recognition processing layer 304 to the first input layer 301 or the second input layer 302 via the intermediate layers 303 (error backpropagation described later).

In the state illustrated in FIG. 5A, the first feature quantity based on the feature quantity output from the first input layer 301 is input to the intermediate layer 303 and the first intermediate feature quantity is calculated in the intermediate layer 303 (first intermediate feature quantity calculation process, first intermediate feature quantity calculation step). FIGS. 6A and 6B are diagrams illustrating how a feature quantity to be input to the intermediate layer 303 is switched. FIG. 6A illustrates a state in which the first feature quantity is input to the intermediate layer 303 (outputs from nodes 301A constituting the first input layer 301 are input to nodes 303A constituting the intermediate layer 303). At the time of inputting, the feature quantity output from the first input layer 301 may be input, as the first feature quantity, to the intermediate layer 303 without any processing, or a feature quantity appropriately multiplexed by a weight may be input, as the first feature quantity, to the intermediate layer 303 (see FIG. 7A). Note that a solid line in FIGS. 6A and 6B indicates a state in which data is output or input from a node as a result of output switching described above, and a dotted line in FIGS. 6A and 6B indicates a state in which data is not output or input from a node. The nodes 301A and 303A are conceptually illustrated, and the numbers thereof are not particularly limited. These points also apply to FIGS. 7A and 7B.

Figure 7A:
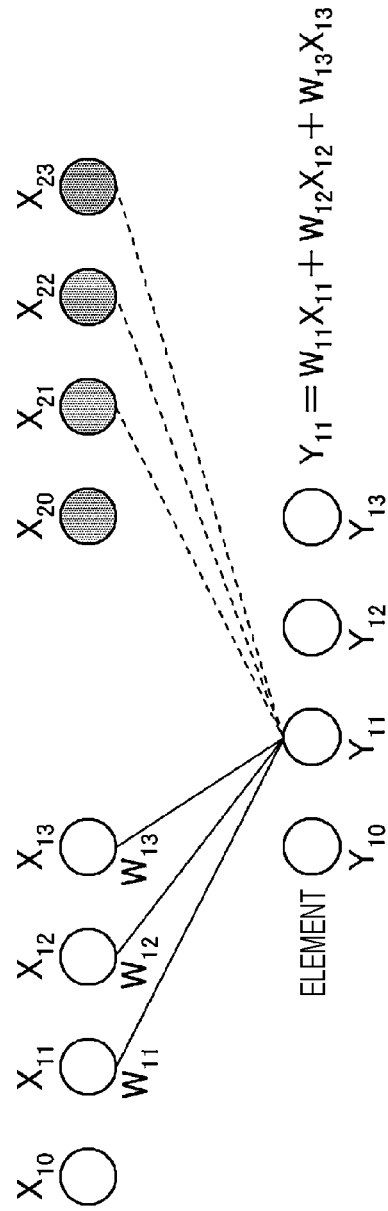
FIGS. 7A and 7B are diagrams illustrating how convolution is performed in the intermediate layer.
Figure 7B:
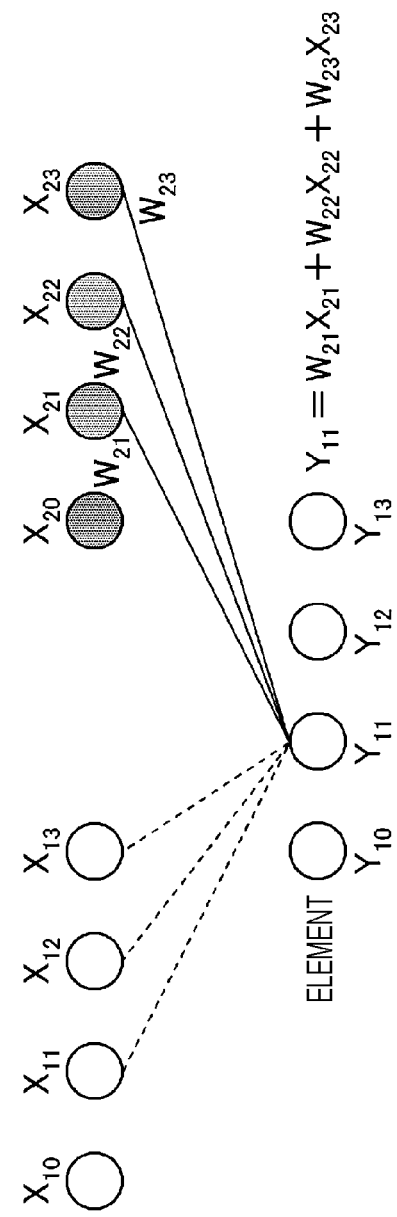

FIGS. 7A and 7B are diagrams illustrating how convolution is performed when feature quantities are input from the first input layer 301 and the second input layer 302 to the intermediate layer 303. FIG. 7A illustrates a state in which outputs of nodes $X_{11}$, $X_{12}$, and $X_{13}$ of the first input layer 301 are respectively multiplied by weight parameters $W_{11}$, $W_{12}$, and $W_{13}$ and the results are input to a node $Y_{11}$ of the intermediate layer 303 (in the state illustrated in FIG. 7A, the output is not input to the node $Y_{11}$ from a node $X_{10}$). FIG. 7A illustrates the input relationships between the nodes $X_{11}$, $X_{12}$, and $X_{13}$ and the node $Y_{11}$. The similar relationships are established also for other nodes $Y_{10}$, $Y_{12}$, and $Y_{13}$ of the intermediate layer 303.

<Output of Recognition Result>

The first intermediate feature quantity calculated in the intermediate layer 303 is input to the recognition processing layer 304, and the recognition processing layer 304 outputs the recognition result.

<Updating of Weight Parameters Through Error Backpropagation>

The error calculation unit 164 compares the recognition result output by the recognition processing layer 304 with the correct answer for the first data to calculate a loss (error), and updates the weight parameters in the first input layer 301 and the intermediate layers 303 from the layer on the output side toward the layer on the input side as illustrated in FIG. 5A (error backpropagation) so that the loss decreases.

<Second Intermediate Feature Quantity Calculation Process>

Since the second intermediate feature quantity calculation process (second intermediate feature quantity calculation step) can be performed in substantially the same manner as the first intermediate feature quantity calculation process, differences from the first intermediate feature quantity calculation process will be mainly described. In the second intermediate feature quantity calculation process, a mini-batch is formed using a plurality of images (second data) selected from among the plurality of special-light images recorded in the second image database 202, and the mini-batch is input to the second input layer 302. At this time, the output is switched as illustrated in FIG. 5B, so that the output from the second input layer 302 is input to the intermediate layer 303. FIG. 6B is a diagram illustrating a state in which the second feature quantity is input to the intermediate layer 303 (outputs from nodes 302A constituting the second input layer 302 are input to the nodes 303A constituting the intermediate layer 303). In the state illustrated in FIG. 5B, the second feature quantity based on the feature quantity output from the second input layer 302 is input to the intermediate layer 303 and the second intermediate feature quantity is calculated in the intermediate layer 303 (second intermediate feature quantity calculation process, second intermediate feature quantity calculation step). FIG. 6B illustrates a state in which the second feature quantity is input to the intermediate layer 303.

Similarly to FIG. 7A, FIG. 7B illustrates a state in which outputs of nodes $X_{21}$, $X_{22}$, and $X_{23}$ of the second input layer 302 are respectively multiplied by weight parameters $W_{21}$, $W_{22}$, and $W_{23}$ and the results are input to the node $Y_{11}$ of the intermediate layer 303 (in the state illustrated in FIG. 7B, the output is not input to the node $Y_{11}$ from a node $X_{20}$). FIG. 7B illustrates the input relationships between the nodes $X_{21}$, $X_{22}$, and $X_{23}$ and the node $Y_{11}$. The similar relationships are established also for the other nodes $Y_{10}$, $Y_{12}$, and $Y_{13}$ of the intermediate layer 303.

The second intermediate feature quantity calculated in the intermediate layer 303 is input to the recognition processing layer 304, and the recognition processing layer 304 outputs the recognition result. As in the case of the normal-light images (first data) described above, the error calculation unit 164 updates the weight parameters through error backpropagation (see FIG. 5B).

<Examples of Learning Patterns>

In the learning system 10, each of the first intermediate feature quantity calculation process (first intermediate feature quantity calculation step) and the second intermediate feature quantity calculation process (second intermediate feature quantity calculation step) is performed at least once. An example of the number of times the processes are performed and the order in which the processes are performed will be described below.

First Example

Figure 8A:
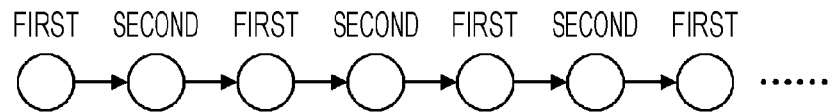
FIGS. 8A to 8C are diagrams illustrating patterns of a first intermediate feature quantity calculation process and a second intermediate feature quantity calculation process.

In a first example, a feature quantity extraction process performed in the first input layer 301 and the first intermediate feature quantity calculation process (first intermediate feature quantity calculation step) subsequent to this are performed at least twice. A feature quantity extraction process performed in the second input layer 302 and the second intermediate feature quantity calculation process (second intermediate feature quantity calculation step) subsequent to this are performed in a period from an end of the first intermediate feature quantity calculation process once to a start of the other first intermediate feature quantity calculation process. For example, the processes are repeated in the order illustrated in FIG. 8A. In FIG. 8A, "FIRST" and "SECOND" respectively represent "the feature quantity extraction process performed in the first input layer 301 and the first intermediate feature quantity calculation process subsequent to this" and "the feature quantity extraction process performed in the second input layer 302 and the second intermediate feature quantity calculation process subsequent to this", which are counted once, twice, . . . , in units of minibatches.

Second Example

Figure 8B:
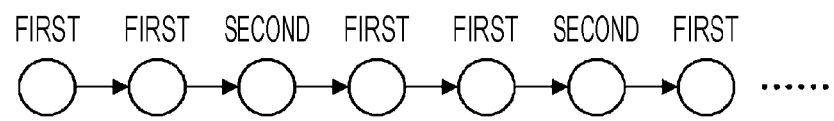
Figure 8C:
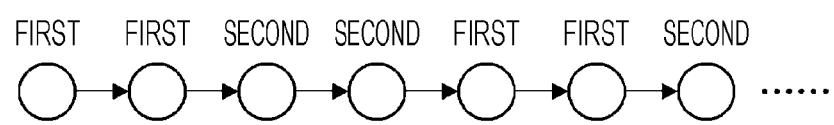
Figure 9:
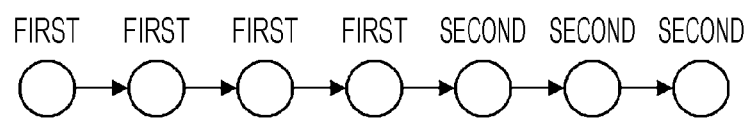
FIG. 9 is a diagram illustrating another pattern of the first intermediate feature quantity calculation process and the second intermediate feature quantity calculation process.

In a second example, the feature quantity extraction process performed in the first input layer 301 and the first intermediate feature quantity calculation process subsequent to this are performed at least twice. After the first intermediate feature quantity calculation process is ended at least twice, the feature quantity extraction process performed in the second input layer 302 and the second intermediate feature quantity calculation process subsequent to this are performed. For example, the processes are repeated in the order illustrated in FIG. 8B. "FIRST" and "SECOND" in FIG. 8B have the same meanings as those in FIG. 8A. In this case, the second intermediate feature quantity calculation process may be successively performed twice as illustrated in FIG. 8C. Alternatively, the feature quantity extraction process performed in the first input layer 301 and the first intermediate feature quantity calculation process subsequent to this may be successively performed a plurality of times. After the first intermediate feature quantity calculation process is ended, the feature quantity extraction process performed in the second input layer 302 and the second intermediate feature quantity calculation process subsequent to this may be performed (see FIG. 9). Note that the patterns illustrated in FIGS. 8A to 9 are merely illustrative, and learning can be performed in various other patterns.

<Advantageous Effects of Embodiment>

In the learning system 10 according to the embodiment, first data and second data are respectively input to the first input layer 301 and the second input layer 302 independent of the first input layer 301, and feature quantities are calculated in the respective input layers. Thus, the feature quantity calculation in one of the input layers is not affected by the feature quantity calculation in the other input layer. In addition, in the learning system 10, in addition to the feature extraction performed in the input layers, each of the first intermediate feature quantity calculation process and the second intermediate feature quantity calculation process is performed at least once in the intermediate layer 303 shared by the first input layer 301 and the second input layer 302. Thus, the feature quantity calculated in each of the input layers can be reflected in the intermediate feature quantity calculation in the intermediate layer 303. Since the hierarchical network involves many parameters, overlearning is likely to occur. However, in the learning system 10 according to the embodiment, learning can be performed in the intermediate layer 303 using a large amount of data including both the first data and the second data. Thus, overlearning is unlikely to occur. On the other hand, since the input layer is configured as the first input layer and the second input layer which are independent of each other, the number of parameters of each input layer reduces. Thus, overlearning is unlikely to occur even with a small amount of data. Accordingly, in the learning system 10, pieces of data (of normal-light images, special-light images, and the like) that belong to the same category and are acquired under different conditions can be appropriately learned.

<Learning Using Combined Minibatch>

In the learning patterns described above, the feature quantities are calculated separately for the first data and the second data in units of minibatches. Alternatively, a first minibatch and a second minibatch may be combined into a single minibatch immediately before the minibatch is input to the intermediate layer 303. Specifically, a minibatch (first minibatch) is formed using a plurality of images (first data) selected from among the plurality of normal-light images recorded in the first image database 201, and the minibatch is input to the first input layer 301 to calculate a feature quantity. In addition, a minibatch (second minibatch) is formed using a plurality of images (second data) selected from among the plurality of special-light images recorded in the second image database 202, and the minibatch is input to the second input layer 302 to calculate a feature quantity. The first minibatch and the second minibatch may be combined for these feature quantities into a single minibatch immediately before the input to the intermediate layer 303, and the combined minibatch is input to the intermediate layer 303.

<Recognition Process>

In the recognition (inference) process, recognition may be performed in a configuration in which either the first input layer 301 or the second input layer 302 is disconnected. For example, in a state in which the second input layer 302 is disconnected and the first input layer 301 alone is connected as illustrated in FIG. 5A, recognition can be performed for the first data and the second data (in this case, both the first data and the second data are input to the first input layer 301). In addition, in a state in which the first input layer 301 is disconnected and the second input layer 302 alone is connected as illustrated in FIG. 5B, recognition can be performed for the first data and the second data (in this case, both the first data and the second data are input to the second input layer 302).

<Learning Using First Narrow-Band-Light Images and Second Narrow-Band-Light Images>

In the example described above, learning using normal-light images (white-light images) and special-light images (for example, blue special-light images) has been described. However, learning may be performed using a plurality of narrow-band-light images for which wavelength balances of the observation light are different. The first input layer may receive, as first image data, first medical image data acquired using first narrow-band light as first observation light. The second input layer may receive, as second image data, second medical image data acquired using, as second observation light, second narrow-band light different from the first narrow-band light. In this case, as the narrow-band light combination, blue light in a plurality of narrow bands, a combination of blue light in a narrow band and violet light in a narrow band, red light in a plurality of narrow bands, or the like can be used.

<Learning Using Other Data>

In the embodiment, learning using endoscopic images acquired using different kinds of observation light has been described. However, with the learning apparatus and the learning method according to the present invention, learning can be performed similarly in the case where medical images other than the endoscopic images, such as images acquired by a computed tomography (CT) apparatus, a magnetic resonance imaging (MM) apparatus, or the like, are used. In addition, learning can be performed similarly even in the case where images other than medical images (other images of, for example, persons, animals, or sceneries) are used. Further, learning can be performed similarly also in the case where the input data is not of images but is of text, sound, or the like.

Although the embodiments of the present invention have been described above, the present invention is not limited to the above-described embodiments, and various modifications can be made within a scope not departing from the spirit of the present invention.

REFERENCE SIGNS LIST 10 learning system
100 learning recognition apparatus
110 image acquisition unit
120 operation unit
130 control unit
140 display unit
142 monitor
150 recording unit 160 processing unit
162 CNN
164 error calculation unit
201 first image database
202 second image database
301 first input layer
301A node
302 second input layer
302A node
303 intermediate layer
303A node
304 recognition processing layer
$W_{11}$ weight parameter
$W_{12}$ weight parameter
$W_{13}$ weight parameter
$W_{21}$ weight parameter
$W_{22}$ weight parameter
$W_{23}$ weight parameter
$X_{10}$ node
$X_{11}$ node
$X_{12}$ node
$X_{13}$ node
$X_{20}$ node
$X_{21}$ node
$X_{22}$ node
$X_{23}$ node
$Y_{10}$ node
$Y_{11}$ node
$Y_{12}$ node
$Y_{13}$ node

What is claimed is:

1. A learning apparatus comprising
a convolution neural network (CNN), the CNN including
a first input layer that receives first data and outputs a feature quantity, the first data being data selected from a first data group constituted by a plurality of pieces of data acquired under a first condition,
a second input layer that is independent of the first input layer and that receives second data and outputs a feature quantity, the second data being data selected from a second data group constituted by a plurality of pieces of data which belong to a category identical to a category of the pieces of data constituting the first data group and which are acquired under a second condition different from the first condition, and
a plurality of intermediate layers in which a first one intermediate layer of the plurality of intermediate layers is shared by the first input layer and the second input layer and receives the feature quantity output by the first input layer and the feature quantity output by the second input layer and calculates another feature quantity, wherein
each of a first intermediate feature quantity calculation process and a second intermediate feature quantity calculation process is performed at least once, the first intermediate feature quantity calculation process being a process in which a first feature quantity based on the feature quantity output from the first input layer is input to the intermediate layer and a first intermediate feature quantity is calculated in the intermediate layer, the second intermediate feature quantity calculation process being a process in which a second feature quantity based on the feature quantity output from the second input layer is input to the intermediate layer and a second intermediate feature quantity is calculated in the intermediate layer.

2. The learning apparatus according to claim 1, wherein the first intermediate feature quantity calculation process is performed at least twice, and the second intermediate feature quantity calculation process is performed in a period from an end of the first intermediate feature quantity calculation process to a start of the other first intermediate feature quantity calculation process.

3. The learning apparatus according to claim 1, wherein the first intermediate feature quantity calculation process is performed at least twice, and the second intermediate feature quantity calculation process is performed after the first intermediate feature quantity calculation process ends at least twice.

4. The learning apparatus according to claim 1, wherein the hierarchical network is a convolutional neural network.

5. The learning apparatus according to claim 1, wherein at least one of the first input layer and the second input layer calculates the feature quantity through a convolutional operation.

6. The learning apparatus according to claim 1, wherein at least one of the first input layer and the second input layer calculates the feature quantity through a pooling process.

7. The learning apparatus according to claim 1, wherein at least one of the first input layer and the second input layer calculates the feature quantity through a batch normalization process.

8. The learning apparatus according to claim 1, wherein the intermediate layer calculates the feature quantity through a convolutional operation.

9. The learning apparatus according to claim 1, wherein the intermediate layer calculates the feature quantity through a pooling process.

10. The learning apparatus according to claim 1, wherein the intermediate layer calculates the feature quantity through a batch normalization process.

11. The learning apparatus according to claim 1, wherein
the first input layer receives, as the first data, first image data acquired under the first condition, and
the second input layer receives, as the second data, second image data acquired under the second condition different from the first condition.

12. The learning apparatus according to claim 11, wherein the first condition and the second condition are different in at least one of an imaging device, a wavelength balance of observation light, a resolution, or image processing to be performed on an image.

13. The learning apparatus according to claim 12, wherein
the first input layer receives, as the first image data, first medical image data acquired using first observation light, and
the second input layer receives, as the second image data, second medical image data acquired using second observation light different from the first observation light in the wavelength balance.

14. The learning apparatus according to claim 13, wherein
the first input layer receives, as the first image data, the first medical image data acquired using white light as the first observation light, and
the second input layer receives, as the second image data, the second medical image data acquired using narrowband light as the second observation light.

15. The learning apparatus according to claim 13, wherein
the first input layer receives, as the first image data, the first medical image data acquired using first narrowband light as the first observation light, and
the second input layer receives, as the second image data, the second medical image data acquired using, as the second observation light, second narrow-band light different from the first narrow-band light.

16. A learning method for a learning apparatus comprising a convolution neural network (CNN), the CNN including
   a first input layer that receives first data and outputs a feature quantity, the first data being data selected from a first data group constituted by a plurality of pieces of data acquired under a first condition,
   a second input layer that is independent of the first input layer and that receives second data and outputs a feature quantity, the second data being data selected from a second data group constituted by a plurality of pieces of data which belong to a category identical to a category of the pieces of data constituting the first data group and which are acquired under a second condition different from the first condition, and
   a plurality of intermediate layers in which a first one intermediate layer of the plurality of intermediate layers is shared by the first input layer and the second input layer and receives the feature quantity output by the first input layer and the feature quantity output by the second input layer and calculates another feature quantity, the learning method comprising:
   a first feature quantity calculation step of inputting a first feature quantity based on the feature quantity output from the first input layer to the intermediate layer and calculating a first intermediate feature quantity in the intermediate layer; and
   a second intermediate feature quantity calculation step of inputting a second feature quantity based on the feature quantity output from the second input layer to the intermediate layer and calculating a second intermediate feature quantity in the intermediate layer, wherein
   each of the first intermediate feature quantity calculation step and the second intermediate feature quantity calculation step is performed at least once.

* * * * *